United States Patent [19]

Tsoucalas

[11] Patent Number: 4,906,453

[45] Date of Patent: Mar. 6, 1990

[54] MOUSSE PRODUCT

[75] Inventor: Michael C. Tsoucalas, Bergenfield, N.J.

[73] Assignee: Jumpeer Nails, Inc., Upper Montclair, N.J.

[21] Appl. No.: 263,976

[22] Filed: Oct. 26, 1988

Related U.S. Application Data

[63] Continuation of Ser. No. 895,656, Aug. 12, 1986, abandoned.

[51] Int. Cl.$^4$ .................. A61K 7/04; A61K 7/043
[52] U.S. Cl. ................................. 424/47; 424/61; 514/773
[58] Field of Search .................... 424/45, 47, 61

[56] References Cited

U.S. PATENT DOCUMENTS

| | | | |
|---|---|---|---|
| 4,201,235 | 5/1980 | Ciavatta | 424/47 |
| 4,567,038 | 1/1986 | Ciaudelli et al. | 424/60 |
| 4,610,874 | 9/1986 | Matravers | 424/70 |

FOREIGN PATENT DOCUMENTS 134964  3/1985  European Pat. Off. .............. 424/45

*Primary Examiner*—Dale R. Ore
*Attorney, Agent, or Firm*—Blum Kaplan

[57] ABSTRACT

A mousse product prepared from a composition including at least water, a drying agent and an emulsifier is provided. The composition is maintained under pressure in an aerosol container and is dispensed from the container as a foam onto wet enameled nails under the action of a propellant. The mousse product dries the wet nail enamel and can then be massaged into the skin to act as a conditioning agent.

16 Claims, 1 Drawing Sheet

MOUSSE PRODUCT

This is a continuation of application Ser. No. 895,656, filed Aug. 12, 1986, now abandoned.

BACKGROUND OF THE INVENTION

This invention relates to mousse products and, in particular, to a mousse product that is useful for shortening the drying time of nail enamel.

Since time immemorial, women have applied nail enamel to their fingernails and toenails for ornamental purposes. While nail enamel is generally considered to beautify the nails, application of the enamel is time-consuming and inconvenient. Specifically, the most time-consuming and inconvenient aspect of the application is the time it takes for the nail enamel to dry. Drying time is generally a minimum of fifteen minutes. During this fifteen minute period, a woman must take care not to permit the wet enamel on the nails to come into contact with any object or substance.

Accordingly, it is desirable to provide a mousse product that can be applied to enameled nails in order to shorten the drying time of the enamel.

SUMMARY OF THE INVENTION

Generally speaking, in accordance with the invention a mousse product that can be applied to the nails following the application of nail enamel in order to shorten the drying time of the nail enamel is provided. The mousse product is prepared from a composition including at least water, a drying agent such as an alcohol, and an emulsifier that also serves as a conditioning agent. Other beneficial additives are also optionally included in the mousse product composition. The composition is maintained under pressure in an aerosol container and is forced out as a foam under the action of a propellant such as isobutane and/or propane. When applied to wet enameled nails, the mousse product serves both to dry the enamel and to condition the nails and cuticles.

It is, therefore, an object of the invention to provide a mousse product that is useful for shortening the drying time of wet nail enamel.

It is a further object of the invention to provide a mousse product that has a conditioning effect for nails and cuticles.

Still other objects and advantages of the invention will in part be obvious and will in part be apparent from the specification.

The invention accordingly comprises a composition of matter possessing the characteristics, properties, and the relation of constituents which will be exemplified in the composition hereinafter described, and the scope of the invention will be indicated in the claims.

DESCRIPTION OF THE DRAWINGS

For a fuller understanding of the invention, reference is had to the following description taken in connection with the accompanying drawings, in which.

DETAILED DESCRIPTION OF THE INVENTION

Figure 1:
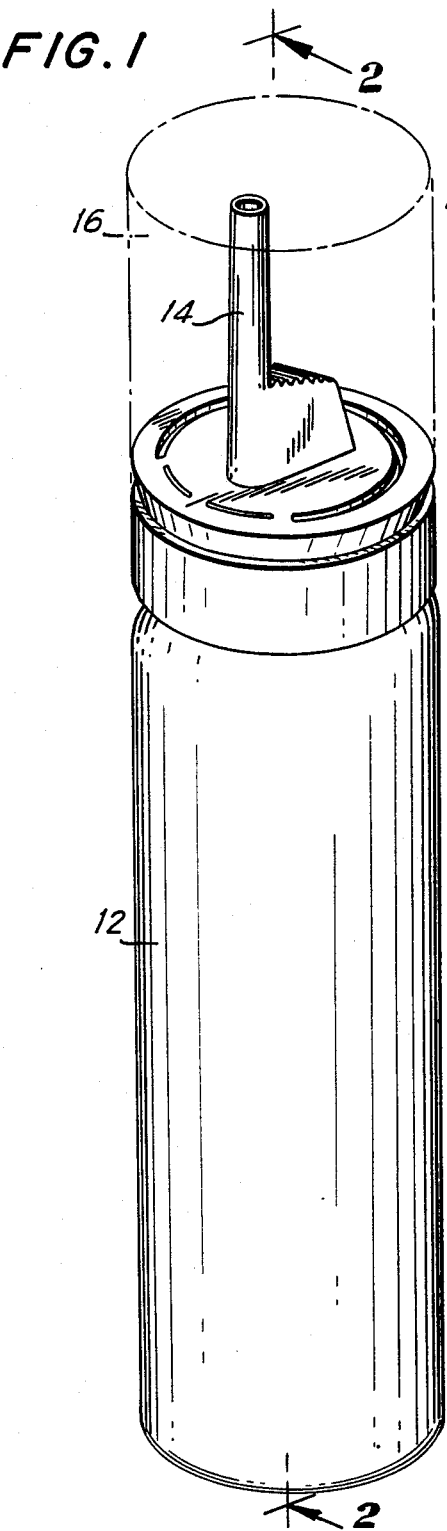
FIG. 1 is a perspective view of an aerosol container adapted to be used in accordance with the present invention.

A nail drying mousse product that can be applied to the nails of one hand in one continuous application as a soft moist foam is provided. The nail drying mousse product is applied directly to nails having wet nail enamel thereon and serves to condition the cuticles while reducing the time it takes for the wet enamel on nails to dry. As the nail enamel dries, the mousse product breaks up to a liquid conditioner. The liquid can then be worked into the skin of the cuticles and hands and into the nails until the skin and fingertips are dry to the touch and conditioned.

In order to accomplish these results, a mousse product prepared from a composition including at least water, a drying agent such as alcohol and an emulsifier that also serves as a conditioning agent is provided. The mousse composition is maintained under pressure in the dispensing compartment of an aerosol container and is forced out of the container as a mousse product under the action of a propellant such as isobutane and/or propane. Other beneficial additives are also optionally included in the mousse composition.

The water used in the mousse composition is preferably purified water and is used in an amount between about 50 and 80% of the total weight of the composition and the propellant. All percentage ranges are of the total weight of the composition and the propellant.

A second solvent, such as an alcohol, is also used and serves as a drying agent. This solvent must be chosen so that the final mousse composition will not interfere with wet nail enamel. In addition, the drying agent must reduce the density of the mousse.

Suitable drying agents include alcohols having less than about eight carbon atoms. Such alcohols include, but are not limited to, ethanol, isopropanol, propylene glycol, butylene glycol, hexylene glycol and dipropylene glycol. In an especially preferred embodiment, ethanol is used. The amount of the second solvent or drying agent is always less than the amount of water and is preferably between about 20 and 40% of the composition and propellant.

An emulsifier is also a required constituent of the mousse composition. The emulsifier also serves as a conditioning agent. In a preferred embodiment, the emulsifier or conditioning agent is Quaternium-26, which is also known as mink amido-propyl dimethyl 2-(hydroxyethyl) ammonium chloride and, alternatively, as (hydroxyethyl) dimethyl (3-mink oil amido-propyl) chloride. The emulsifier or conditioning agent is used in an amount between about 0.1 and 4% of the composition and propellant.

In addition to foam stabilization, Quaternium-26 supplies an even deposit of fatty acid groups derived from mink oil. The cationic charged moeity helps deposit this conditioning agent along the cuticle and nail surface together with the highly refined mink oil.

In an exemplary embodiment of the invention, Polyquaternium-4 is used in addition to the Quaternium-26. This combination of conditioners is a cationic combination that is both substantive and conditioning. In addition, the combination does not interfere with wet nail enamel. Furthermore, use of both of these quaternary emulsifiers gives stability to the resultant foam. When Polyquaternium-4 is used in addition to the Quaternium-26, it is used in amounts between about 0.1 and 2% of the composition and propellant.

Other copolymers of a hydroxyethyl-cellulose type that are quaternized with an ammonium chloride charge may be substituted. Exemplary of these copolymers is Polyquaternium-10.

Other beneficial additives are also optionally included in the mousse composition. Such additives include, but are not limited to, fragrance, dditional conditioners and vitamins. An emulsifying wax may also be used. Each of these additives may be used in an amounts between about 0.1 and 2% of the composition and propellant.

In a further exemplary embodiment of the invention, panthenol and vitamin E acetate are used to contribute to the moisturizing, conditioning and healing properties of the resulting mousse product. In addition, hydrolyzed animal protein is used in the form of soluble collagen. Alternatively, the hydrolyzed animal protein is substituted with lecithin or hydrolyzed mucopolysaccharides.

The constituents of the mousse composition are mixed and the composition is poured into the dispensing compartment of an aerosol container. The container is pressurized using a suitable gaseous propellant. The concentration of propellants is chosen so that a balance is struck as the product is delivered from the pressurized system. If the propellant is too rich, a dense, stiff foam will result. This is not a desirable feature in a nail drying mousse.

The container is pressurized with isobutane in an amount between about 2 and 15% and propane in an amount between about 0.2 and 3% of the composition and propellant. The combination isobutane/propane propellant may be substituted with other hydrocarbon propellants. Such other hydrocarbon propellants include, but are not limited to, dimethyl ether, which can be used either by itself or in combination with isobutane/propane. The dimethyl ether may be used in amounts between about 2 and 15% and the isobutane/propane may be used in the ranges specified.

Figure 2:
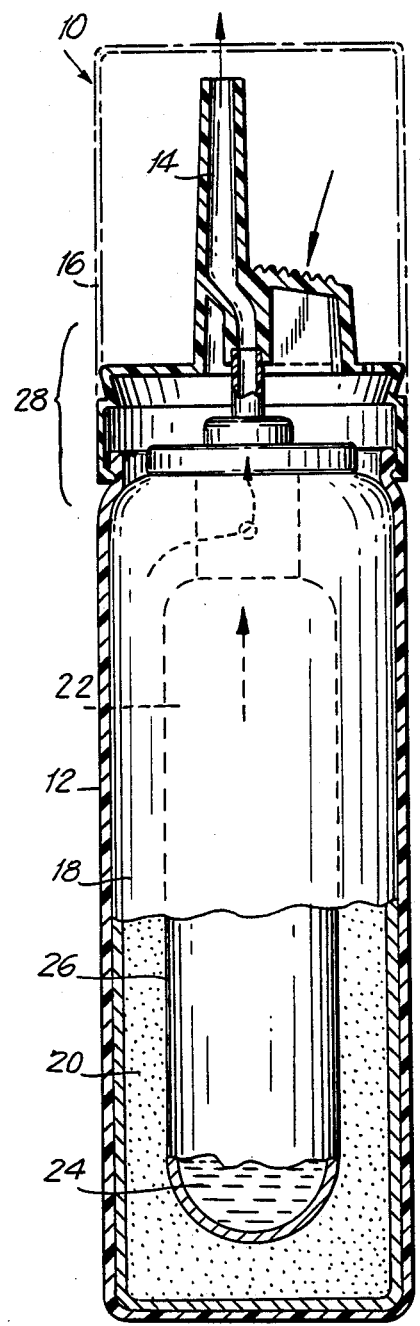
FIG. 2 is a cross-sectional viw of the aerosol container of FIG. 1 taken along section line 2—2 of FIG. 1.

An exemplary aerosol container for use with the mousse product of the invention is shown in FIGS. 1 and 2 and is depicted generally as 10. Container 10 has a body 12, a spout 14 and cap 16. The interior walls of body 12 define a propellant reservoir 18 which is adapted to contain a gaseous propellant 20 shown in cut-away cross-section in FIG. 2. Dispensing compartment 22 is provided as a separate compartment within the boundaries of propellant reservoir 18. In general, walls 26 of dispensing compartment 22 are gas permeable, but not liquid permeable. The liquid mousse composition of the invention 24 is contained in dispensing compartment 22. A nozzle 28 is provided for the purpose of forcing liquid composition 24 out of container 10 under the action of propellant 20 in such a way as to mix liquid composition 24 with propellant 20 in a predetermined proportion. In use, dispensing compartment 22 is first filled with liquid composition 2 and then the container 10 is pressurized by forcing a gaseous propellant 20 into propellant reservoir 18. Spout 14 may be any desired size or shape, but the one shown has been found to be especially desirable for applying a foam mousse product to wet enameled nails. It is to be understood that aerosol containers are well known in the art and the invention is not intended to be limited by the particular type of container used.

In use, nail enamel is applied to finger or toenails. Following application of the nail enamel, but prior to the time in which the nail enamel is expected to dry, the nail drying mousse is dispensed from the aerosol container directly onto the wet enameled nails. After a short period of time, the nail mousse breaks down to a liquid and can be massaged into the skin of the hands or feet and into the cuticles. Once this is accomplished, the nail enamel will be dry to the touch and the cuticles and skin will be conditioned. A finishing top coat may be applied over the treated nails, if desired.

The nail mousse of the present invention will be described further with reference to the following Examples. These Examples are presented for purposes of illustration only and are not intended to be construed in a limiting sense.

EXAMPLE 1

A nail mousse product was prepared using the following ingredients in the proportions shown. All percentages are by weight.

| Water | 59.75% |
|---|---|
| Alcohol | 25.00% |
| Quaternium-26 | .25% |

These ingredients were mixed and poured into the dispensing compartment of an aerosol container. The container was pressurized using isobutane in an amount of 13.5% and propane in an amount of 1.5%.

EXAMPLE 2

A nail mousse product was prepared using the following ingredients in the proportions shown. All percentages are by weight.

| Water | 64.05% |
|---|---|
| SD Alcohol 40 | 32.00% |
| Quaternium-26 | .25% |
| Fragrance | .20% |
| Panthenol | .10% |
| Hydrolyzed Animal Protein | .10% |
| Tocopheryl Acetate | .10% |
| Mink Oil | .10% |
| Polyquaternium-4 | .10% |

These ingredients were mixed and poured into the dispensing compartment of an aerosol container. The container was pressurized using isobutane in an amount of 2.7% and propane in an amount of 0.3%.

The mousse compositions were dispensed from the aerosol containers onto wet enameled nails two minutes after the application of nail enamel to the nails. The compositions were dispensed from the containers as soft moist foam which immediately began to break up to a liquid. The liquid was massaged into the skin and cuticles. The liquid was completely massaged within four minutes after application of the nail enamel to the nails and the nail enamel was completely dry and the cuticles and skin were conditioned.

It will thus be seen that the objects set forth above, among those made apparent from the preceding description, are efficiently attained and, since certain changes may be made in the above composition of matter without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A nail drying mousse product prepared by the process comprising the steps of:
    preparing a composition comprising between about 50 and 80% by weight of water, between about 20 and 40% by weight of an alcohol having less than 8 carbon atoms and between about 0.1 and 4.0% by weight of Quaternium-26;
    filling a dispensing compartment of an aerosol container with the composition;
    pressurizing the compartment using a gaseous hydrocarbon propellant; and
    dispensing the composition from the container under the action of the propellant to provide the mousse product.

2. A product of claim 1, wherein the alcohol is selected from the group consisting of ethanol, isopropanol, propylene glycol, butylene glycol, hexylene glycol and dipropylene glycol.

3. The product of claim 1, wherein the composition further includes between about 0.1 and 2% by weight of Polyquaternium-4 as a conditioning agent.

4. The product of claim 1, wherein the composition further includes between about 0.1 and 2% of at least one additive selected from the group consisting of panthenol, vitamin E acetate, soluble collagen, lecithin and hydrolyzed mucopolysaccharides.

5. The product of claim 1, wherein the hydrocarbon propellants are isobutane and propane.

6. The product of claim 5, wherein isobutane is used in an amount between about 2 and 15% by weight of the composition and propellant and propane is used in an amount between 0.2 and 3% by weight of the composition and propellant.

7. A nail drying mousse composition comprising between about 50-80% by weight of water, between about 20-40% by weight of a drying agent and between about 0.1-4% by weight of Quaternium-26 and containing a hydrocarbon propellant.

8. A nail drying mousse product prepared by the process comprising the steps of:
    preparing a composition containing between about 50 and 80% by weight of water, between about 20 and 40% by weight of SD Alcohol 40, between about 0.1 and 4.0% by weight of Quaternium-26, between about 0.1 and 2% by weight of fragrance, between about 0.1 and 2% by weight of panthenol, between about 0.1 and 2% by weight of hydrolyzed animal protein selected from the group consisting of soluble collagen, lecithin and hydrolyzed mucopolysaccharides, between about 0.1 and 2.0% by weight of tocpheryl acetate, about 0.1% by weight of mink oil and between about 0.1 and 2% by weight of polyquaternium-4;
    filling a dispensing compartment of an aerosol container with the composition;
    pressurizing the compartment using a hydrocarbon propellant; and
    dispensing the composition from the container under the action of the propellant to provide the mousse product.

9. A nail drying mousse product prepared by the process comprising the steps of:
    preparing a composition consisting essentially of between about 50 and 80% by weight of water, between about 20 and 40% by weight of an alcohol having less than 8 carbon atoms and between about 0.1 and 4.0% by weight of Quaternium-26;
    filling a dispensing compartment of an aerosol container with the composition;
    pressurizing the compartment using a gaseous hydrocarbon propellant; and
    dispensing the composition from the container under the action of the propellant to provide the mousse product.

10. A nail drying mousse product prepared by the process comprising the steps of:
    preparing a composition consiting essentially of between about 50 and 80% by weight of water, between about 20 and 40% by weight of SD Alcohol 40, between about 0.1 and 4.0% by weight of Quaternium-26, between about 0.1 and 2% by weight of fragrance, between about 0.1 and 2% by weight of panthenol, between about 0.1 and 2% by weight of hydrolyzed animal protein selected from the group consisting of soluble collagen, lecithin and hydrolyzed mucopolysaccharides, between about 0.1 and 2.0% by weight of tocopheryl acetate about 0.1% by weight of mink oil and between about 0.1 and 2% by weight of polyquaternium-4;
    filling a dispensing compartment of an aerosol container with the composition;
    pressurizing the compartment using a hydrocarbon propellant; and
    dispensing the composition from the container under the action of the propellant to provide the mousse product.

11. A method for drying nail enamel comprising the steps of:
    applying a mousse product prepared from a composition including between about 50-80% by weight of water, between about 20-40% by weight of a drying agent, and between about 0.1-4.0% by weight of Quaternium-26 by using at least one hydrocarbon propellant to foam said composition, to enameled nails;
    allowing the mousse product to break down to a liquid; and,
    massaging the liquid into the nails, cuticles and skin.

12. A nail mousse dispenser comprising, container means including a dispensing compartment, a propellant reservoir and a nozzle means, a composition comprising at least between about 50-80% by weight of water, between about 20-40% by weight of a drying agent and between about 0.1-4% by weight of Quaterium-26 stored in said dispensing compartment, a hydrocarbon propellant stored in said propellant reservoir and said nozzle means adapted to dispense the composition from said dispensing compartment under the action of the propellant so as to create a nail drying mousse when the composition and the propellant are mixed.

13. The dispenser of claim 12, wherein said dispensing compartment is surrounded by said propellant compartment.

14. The dispenser of claim 12, wherein the walls of the propellant compartment are defined by the inner walls of the container means.

15. The dispenser of claim 12, wherein the propellant is gaseous.

16. The dispenser of claim 15, wherein the gaseous propellant is a hydrocarbon product.

* * * * *